United States Patent
Kim et al.

(10) Patent No.: US 9,585,459 B2
(45) Date of Patent: Mar. 7, 2017

(54) VACUUM CONTAINER FOR CREAM TYPE COSMETIC

(71) Applicant: YONWOO CO., LTD., Incheon (KR)

(72) Inventors: You-Seob Kim, Incheon (KR); Ki-Baik Kim, Incheon (KR)

(73) Assignee: YONWOO CO., LTD., Incheon (KR)

( * ) Notice: Subject to any disclaimer, the term of this patent is extended or adjusted under 35 U.S.C. 154(b) by 0 days.

(21) Appl. No.: 14/769,723

(22) PCT Filed: Feb. 12, 2014

(86) PCT No.: PCT/KR2014/001134
§ 371 (c)(1),
(2) Date: Aug. 21, 2015

(87) PCT Pub. No.: WO2014/129767
PCT Pub. Date: Aug. 28, 2014

(65) Prior Publication Data
US 2016/0000206 A1    Jan. 7, 2016

(30) Foreign Application Priority Data

Feb. 25, 2013 (KR) .................. 10-2013-0019593

(51) Int. Cl.
*B43K 5/02* (2006.01)
*A45D 40/00* (2006.01)
(Continued)

(52) U.S. Cl.
CPC ..... *A45D 40/0075* (2013.01); *A45D 40/0068* (2013.01); *A61M 35/003* (2013.01);
(Continued)

(58) Field of Classification Search
CPC ............ A45D 40/0075; B65D 83/0044; B05B 11/0048
(Continued)

(56) References Cited

U.S. PATENT DOCUMENTS 3,760,985 A * 9/1973 Bryan ................ A45D 40/0075
220/529
8,499,970 B2 * 8/2013 Yoo ........................ A45D 34/00
116/227

(Continued)

FOREIGN PATENT DOCUMENTS

| JP | 2012-196445 A | 10/2012 |
|----|----|----|
| KR | 20-0161316 Y1 | 11/1999 |
| KR | 20-0370308 Y1 | 12/2004 |
| KR | 2009-0065146 A | 6/2009 |

OTHER PUBLICATIONS

International Search Report issued in PCT/KR2014/001134 on Apr. 29, 2014.

*Primary Examiner* — Jennifer C Chiang
(74) *Attorney, Agent, or Firm* — Marshall, Gerstein & Borun LLP

(57) ABSTRACT

A vacuum cosmetic container for cream type cosmetics has a feature in that a content absorption member absorbing discharged contents is installed to the upper portion of a button part, so that it is possible to use the contents absorbed in a content absorption member as needed by coating with a hand or a cosmetic applicator and thus to prevent unnecessary consumption of the contents.

4 Claims, 4 Drawing Sheets

(51) Int. Cl.
*B65D 83/00* (2006.01)
*B05B 11/00* (2006.01)
*A61M 35/00* (2006.01)

(52) U.S. Cl.
CPC ...... *B05B 11/0048* (2013.01); *B05B 11/3023* (2013.01); *B05B 11/3045* (2013.01); *B05B 11/3069* (2013.01); *B65D 83/0005* (2013.01); *B65D 83/0044* (2013.01); *A45D 2200/051* (2013.01); *A45D 2200/1018* (2013.01); *B05B 11/0037* (2013.01); *B05B 11/3047* (2013.01); *B05B 11/3074* (2013.01)

(58) Field of Classification Search
USPC .............................................. 401/188 R, 189
See application file for complete search history.

(56) References Cited

U.S. PATENT DOCUMENTS

| | | | |
|---|---|---|---|
| 8,876,422 B2* | 11/2014 | Lim | A45D 34/04 401/188 R |
| 2009/0179048 A1 | 7/2009 | Decottignies et al. | |
| 2012/0006853 A1* | 1/2012 | Lim | A45D 40/0075 222/256 |
| 2012/0085788 A1* | 4/2012 | Lu | A45D 34/04 222/390 |
| 2014/0020706 A1* | 1/2014 | Thiebaut | A45D 19/02 132/314 |
| 2015/0090739 A1* | 4/2015 | Jung | B05B 11/0024 222/205 |

\* cited by examiner (a)

(b)

VACUUM CONTAINER FOR CREAM TYPE COSMETIC

CROSS-REFERENCE TO RELATED APPLICATIONS

This U.S. non-provisional patent application is a national stage application under 35 U.S.C. §371 of international application PCT/KR2014/001134, filed Feb. 12, 2014, and claims the benefit of priority under 35 U.S.C. §119 of Korean Patent Application No. 10-2013-0019593, filed Feb. 25, 2013, the entire contents of which are hereby incorporated herein by reference for all purposes.

TECHNOLOGICAL FIELD

The present disclosure relates to a vacuum container for cream type cosmetics, and more particularly to a vacuum cosmetic container for cream type cosmetics, which, by installing a content absorption member to the upper portion of a button part for absorbing discharged contents and by making it possible to make it possible to use the contents absorbed in a content absorption member as needed by coating with a hand or a cosmetic applicator, can prevent unnecessary consumption of the contents.

The vacuum cosmetic container for cream type cosmetics according to the present disclosure includes a content absorption member attached to the upper portion of a button part for absorbing discharged contents, which make it possible to use the contents absorbed in a content absorption member as needed by coating with a hand or a cosmetic applicator, thus preventing unnecessary consumption of the contents.

BACKGROUND

Generally, cream type cosmetics, such as moisturized cream, massage cream, eye cream, foundation, has a lot of oil, and it is a common knowledge that it can easily be spoiled, compared to low viscosity cosmetics such as skin lotion and lotion. Since these cream-type cosmetics are stored in a container with a wide mouth so as to be taken out a little by a little by hand, it is likely to be oxidized by air contact, and also easily contaminated by foreign substances or moisture on the hand.

To make up for these drawbacks, vacuumed cosmetic containers are widely used to make a certain amount of contents discharged under airtight state. In particular, without being discharged by hand, instead with a plate-shaped button provided are useful, contents can be used after a certain amount of contents is filled.

A traditional vacuum container of these kinds with a plate-shaped button is shown in FIG. 1. Referring FIG. 1, a traditional vacuum container with a plate-shaped button comprises a container body (11) containing contents like cosmetics, a dispenser (12) pumping and discharging a certain amount of contents onto a top portion of the container body, and a button (13) having a plate-shape on an upper portion of the dispenser.

In this configuration, the dispenser (12) comprises a cylinder (14) combined to a top portion of the container body (11) and a piston (17) installed at an inner wall of a suction hole (15) formed on the cylinder (14) so as for the button to repeatedly pump by a spring (16). Furthermore, a check valve (18) is installed at a lower end of the suction hole (15), a piston rod (19) is communicated with the suction hole (15) at the piston (17) and forms an outflow tract for contents to flow out, and a penetrating hole (20) is installed on the button (13), wherein the piston rod (19) is inserted in the middle. In addition, an assisting cap (21), made of soft synthetic resin, is installed on the penetrating hole (20) so as to be elastically deformed by outer pressure and to form a gap.

A vacuum container for cosmetics with a plate-shaped button composed of as the above has a configuration wherein an upper end of a button (13) has a plate-shape which goes deeper as nearer to the center of a top portion, and is formed to use contents by absorbing the contents discharged into a top portion of the button (13) by hand or by an applying tool. By a pumping operation according to pressurization of the button (13), a certain amount of contents is discharged onto a top portion of the button (13); however, since every user needs a different amount of contents, amount of contents by a pumping operation may happen to be more than needed. At this time, the contents which are discharged more than needed may be discarded without being used or unintentionally applied on a skin, thereby leading to unnecessarily consumption of contents and users' excessive cost burdens.

SUMMARY OF THE DISCLOSURE

The presently disclosed embodiments are devised to solve the said problems above, and its goal is to provide a content absorption member attached to the upper portion of a button for absorbing the discharged content, which makes it possible to use the content absorbed in the absorption member as needed by hand or by a cosmetic applying tool, thus preventing unnecessary consumption of the contents.

Furthermore, it is possible for the contents to be absorbed evenly onto the content absorption member by forming many discharging holes on the content absorption member, thereby providing a vacuum container for cream type cosmetics for users' conveniences.

To solve the above problems, it is featured that a vacuum container for cream type cosmetics comprises an outer container; an inner container which is combined to an interior of the outer container and where contents are kept, and a piston ascending upwards according to the use of contents inside is installed; a support body combined as encircling an upper portion of the outer container; supporting a pumping member; a pumping member which is combined to the support body and discharges contents by pumping operation; a button part which is placed on the pumping member and pressurizes the pumping member, wherein a contents movement hole is installed for contents moving along; a content absorption member which is placed on upper portion of the button part and absorbs contents moving along through the contents movement hole; a button cap which encircles the button part and contents absorption member and is combined thereat, wherein a hollow is formed so as for the contents absorption member to be exposed to the outside as delivering pressure to the button part according to a user's pressurization.

Furthermore, it is featured that between the button part and the contents absorption member is installed the contents discharge member, comprising a multitude of contents discharging holes that is communicated with the contents movement hole of the button part and can deliver the contents moving through the contents movement hole to the contents absorption member.

Furthermore, it is featured that on a top portion is installed a pressing part that extends inward and pressurizes a top portion of the contents absorption member, and at a lower end is installed a fixed protrusion which fixes the contents absorption member.

Furthermore, it is featured that the contents absorption member includes one of the followings, a puff, a sponge, a foam, and a brush.

As mentioned above, the presently described embodiments have an advantage wherein on an upper portion of the button part is installed the contents absorption member that absorbs discharged contents, and it is possible to use the contents absorbed in the absorption member as needed by the hand or by a cosmetic applicator, thus preventing unnecessary consumption of the contents.

Furthermore, the presently described embodiments have an advantage that a multitude of the contents discharging hole is installed on the contents discharge member and it is possible for the contents to be absorbed evenly, thereby providing users' convenience.

DETAILED DESCRIPTION

Figure 1:
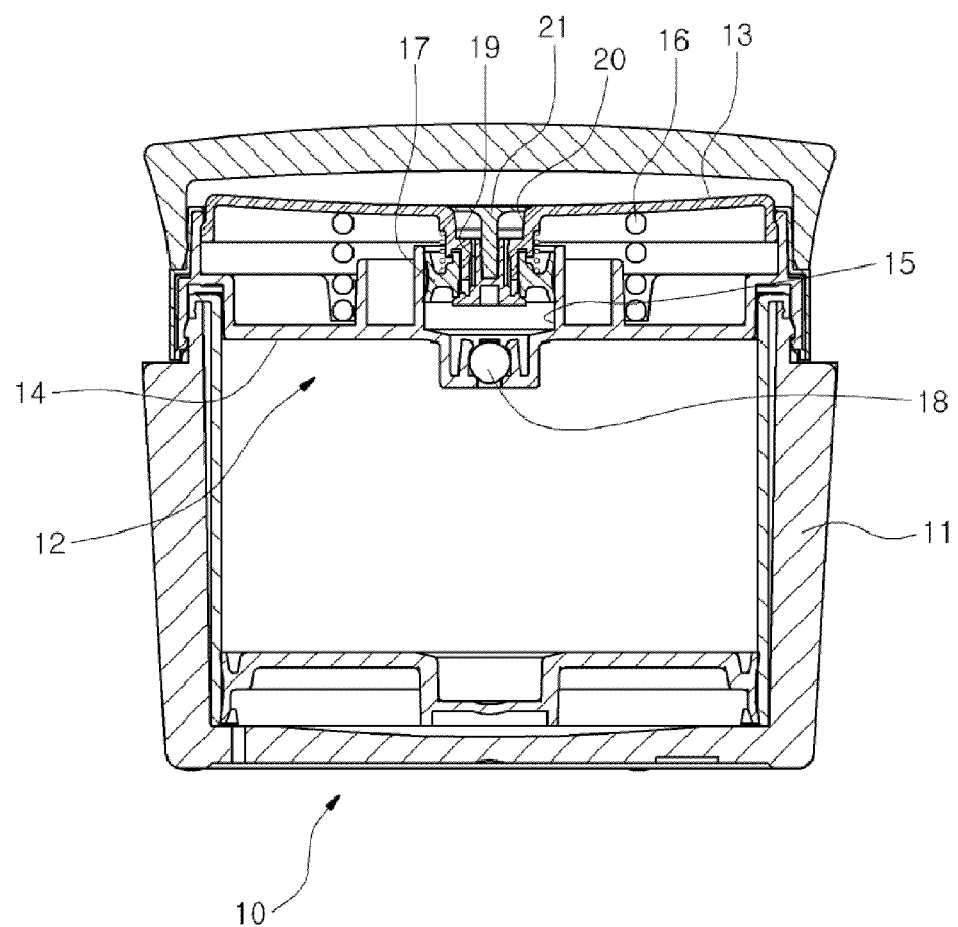
FIG. 1 is a cross-sectional view illustrating a configuration of a traditional cream-type vacuum container.

Hereinafter, exemplary embodiments will be described in detail with reference to the accompanying drawings. The same reference numerals provided in the drawings indicate the same members.

Figure 2:
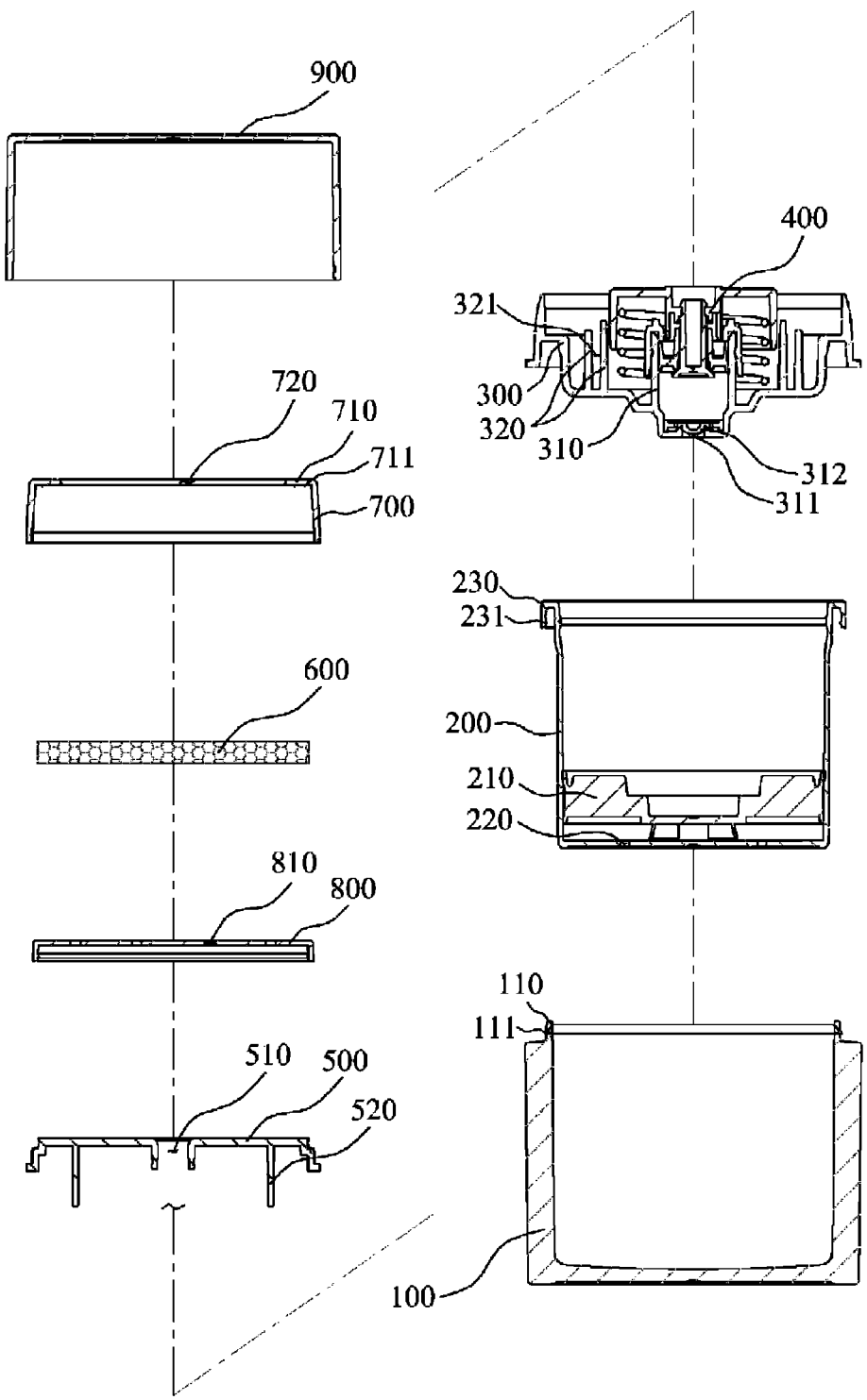
FIG. 2 is an exploded cross-sectional view illustrating a configuration of a vacuum cosmetic container for cream type cosmetics according to an embodiment.
Figure 3:
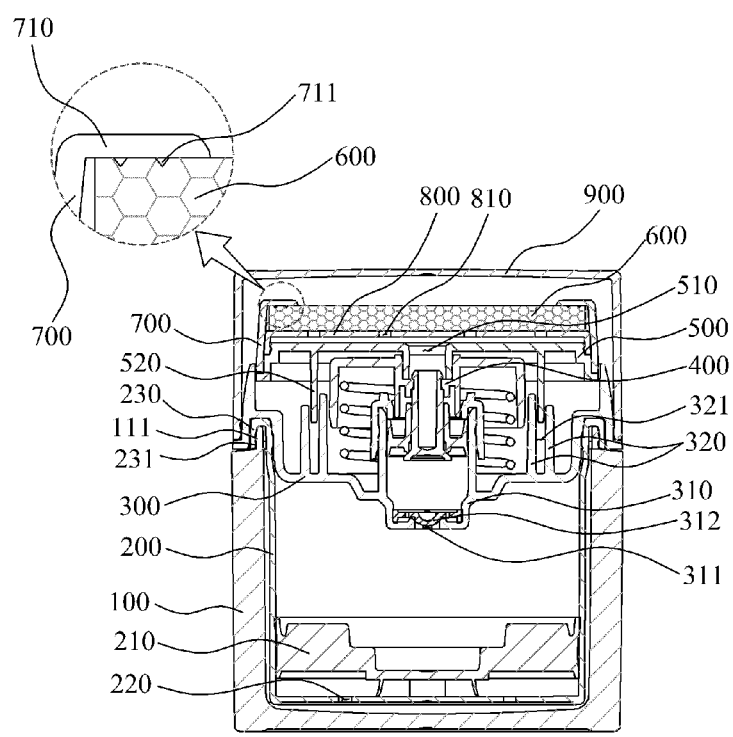
FIG. 3 is an assembled cross-sectional view illustrating a configuration of a vacuum cosmetic container for cream type cosmetics according to an embodiment.
Figure 4:
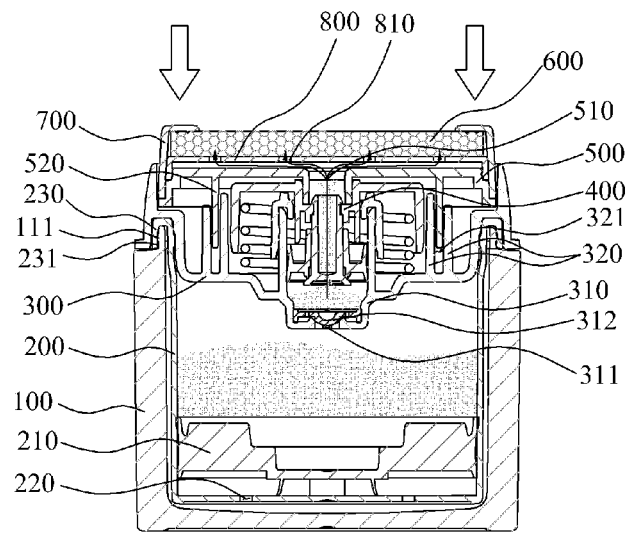
FIG. 4 is a constitutional view illustrating an operational state of a vacuum cosmetic container for cream type cosmetics according to an embodiment.
Figure 4:
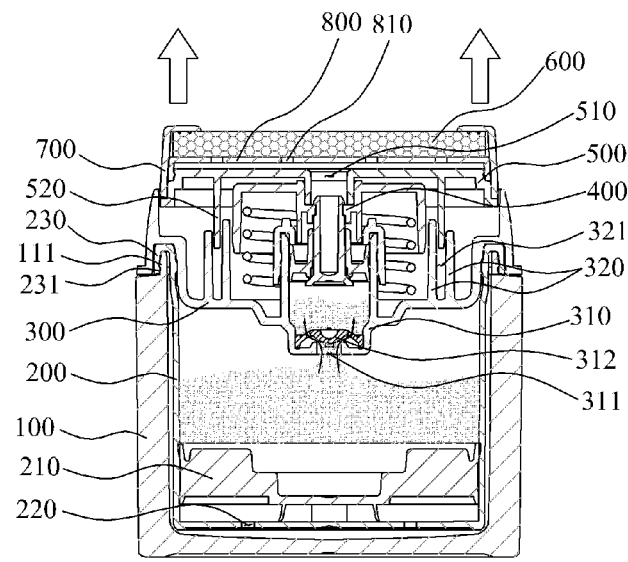

FIG. 2 is an exploded cross-sectional view illustrating a configuration of a vacuum cosmetic container for cream type cosmetics according to an embodiment. FIG. 3 is an assembled cross-sectional view illustrating a configuration of a vacuum cosmetic container for cream type cosmetics according to an embodiment. FIG. 4 is a constitutional view illustrating an operational state of a vacuum cosmetic container for cream type cosmetics according to an embodiment.

Referring to FIGS. 2 to 4, a vacuum cosmetic container for cream type cosmetics according to an embodiment includes an outer container 100, an inner container 200, a support body 300, a pumping member 400, a button part 500, a contents absorption member 600, and a button cap 700.

The outer container 100 holds an inner container 200, on an upper portion of which a combining part 110 comprising a combining protrusion is installed to be combined with the inner container 200 to be explained later.

The inner container 200, which is inserted in the interior of the outer container 110 and where contents are kept, comprises a piston 210 which ascends according to use of the contents inside the inner container 200, wherein an air inflow hole 220 is installed at a lower end of the inner container 200, so that the air flowing in through a space formed by the outer container 100 and the inner container 200 moves into the interior of the inner container 200 and can lift a piston 210.

On an upper portion of the inner container 200 is provided a bent part 230 which is bent to outer direction and combined to a combining part 110, and on the bent part 230 is provided an engaging protrusion 231 which meets the lower end of the combining protrusion 111 so as to be prevented from being separated to upper direction after being combined to the combining part 110 of the outer container body 100.

The support body 300 is combined as encircling the outer container 100 and the inner container 200, and supports a pumping member 400. In the center portion of the support body is provided a cylinder 310, wherein a seal cap, which is combined to a piston rod of the pumping member 400 and an outer circumferential surface of the piston rod, ascends and descend, supporting the pumping member 400. At the lower end of the cylinder 310 is provided a content inflow hole 311 so as for the contents kept in the inner container 200 to flow in when the pumping member operates. At an upper end of the content inflow hole 311 is installed a check valve 312 that opens and closes according to operation or non-operation of the pumping member 400.

Furthermore, at the support body 300 is provided a protrusion 320 which comprises a guide groove 321 so as to prevent distortion and guide vertical movement when the button part 500 ascends and descends.

On the other hand, at the support body 300 is combined an over cap 900 so as to encircle a button cap 700 and thereby to be able to be attached and detached to the support body 300. The over cap 900 is combined as encircling the button cap 700 and thereby prevents malfunction of the pumping member 400 caused by pressurization of the button cap 700.

The pumping member 400 is combined to the support body 300 and discharges contents by pumping operation, as is generally understood.

The button part 500 is combined to an upper portion of the pumping member 400 and pressurizes the pumping member 400 by pressurization of the button cap 700 according to a user's control, thereby enabling pumping operation. On the center of the button part 500, a content movement hole 510 is provided to enable contents to move by pumping operation of the pumping member 400.

At the button part 500 is installed a guide protrusion 520 which moves inside the guide groove 320 and thereby guides vertical movement of the button part 500.

The content absorption member 600 is positioned at an upper portion of the button part 500 and absorbs the contents flowing in through the content movement hole 510, thereby making it possible for a user to apply the contents by hand or by means of a cosmetic applicator, which can be various kinds of materials such as puff, sponge, foam, or brush, preferably made of a porous material for easy absorption of contents.

When an over cap 900 is closed without using up all the absorbed contents, the content absorption member 600 stays in a content-absorbing state, and thereby, when reusing it later, it is possible to use the absorbed contents by hand or by means of a cosmetic applicator without another pumping operation.

When contents absorbed into the content absorption member 600 lacks, the contents can be used by reabsorbing contents into the content absorption member 600 through pumping operation by pressurizing the button cap 700.

The button cap 700 is combined as encircling the button part 500 and the content absorption member 600, and according to a user's pressurization, delivers pressure to the button part 500, thereby making a pumping operation of the pumping member 400 possible, wherein a hollow 720 is formed which exposes the content absorption member 600 so as to make it possible for a user to use the contents absorbed into the content absorption member 600.

At the upper end is installed a pressing part 710 which extends to an inner surface direction so as to prevent the content absorption member 600 from being separated and pressurizes an upper end of the content absorption 600. At a lower end of the pressing part 710, it is preferred that a fixed protrusion 711 is formed to fix the content absorption 600.

On the other hand, between the button part 500 and the content absorption member 600, is installed a content discharge member 800 which is connected with the content movement hole 510 of the button part 500 and delivers contents moving through the content movement hole 510 to the content absorption member 600. At the content discharge member 800 are formed a multitude of content discharge holes 810 evenly positioned with a regular interval.

The content discharge member 800 is preferred to have a space, placed with a narrow margin apart from the button part 500, thereby allowing the contents to move smoothly to a multitude of content discharge holes 810.

In the following, referring to FIG. 4, an operational procedure of a vacuum cosmetic container for cream type cosmetics according to an embodiment will be explained. FIG. 4 is a constitutional view illustrating an operational state of a vacuum cosmetic container for cream type cosmetics according to an embodiment.

Referring to FIG. 4, as for a vacuum cosmetic container for cream type cosmetics according to an embodiment, when a button cap 700 is pressurized, a button part 500 combined to a lower portion of the button cap moves downwards and pumping operation of a pumping member 400 is performed by downward movement of a button part 500, thereby leading contents stored in a cylinder 310 to move to a content discharge member 800 via a content movement hole 5110 of a button part 500 and to be discharged through a multitude of content discharging holes 810 formed at the content discharge member 800.

As the above, when contents are discharged by a multitude of content discharging holes 810, a content absorption member 600 positioned at an upper portion of a content discharge member 800 absorbs contents, and the contents absorbed in a content absorption member 600 can be used by coating with a hand or a cosmetic applicator.

As described above, optimal embodiments have been disclosed in the drawings and the specification. Although specific terms have been used herein, these are only intended to describe the present embodiments and are not intended to limit the meanings of the terms or to restrict the scope of the accompanying claims. Accordingly, those skilled in the art will appreciate that various modifications and other equivalent embodiments are possible from the above embodiments. Therefore, the scope of the claims should be defined by the technical spirit of the specification.

What is claimed is:

1. A vacuum cosmetic container for cream type cosmetics comprising:
    an outer container;
    an inner container, combined at the interior of the outer container and containing contents, inside of which is installed a piston which ascends according to the use of contents;
    a support body combined as encircling an upper portion of the outer container and supporting a pumping member;
    a pumping member combined to the support body and discharging contents by pumping operation;
    a button part positioned at an upper portion of the pumping member and pressurizing the pumping member, wherein a content movement hole is installed;
    a content absorption member positioned at an upper portion of the button part and absorbing contents moving through the content movement hole; and
    a button cap combined as encircling the button part and the content absorption member and delivering pressure to the button part according to a user's pressurizing, wherein a hollow is formed so as for the content absorption member to be exposed to the exterior.

2. The vacuum cosmetic container for cream type cosmetics of claim 1, comprising a content discharge member, wherein a multitude of content discharging holes, connected with the content movement hole of the button part between the button part and the content absorption member, is formed so that contents moving through the content movement hole is delivered to the content absorption member.

3. The vacuum cosmetic container for cream type cosmetics of claim 1, comprising a pressing part which extends to an inner surface direction at an upper end of the button cap and pressurizes an upper end of the content absorption member, and a protrusion which fixes the content absorption member at the lower end of the pressing part.

4. The vacuum cosmetic container for cream type cosmetics of claim 1, wherein the content absorption member can be made of one of materials such as puff, sponge, foam, or brush.

* * * * *